(12) United States Patent
Major et al.

(10) Patent No.: US 9,408,584 B2
(45) Date of Patent: Aug. 9, 2016

(54) METHOD, APPARATUS AND SYSTEM FOR AUTOMATED SPINE LABELING

(71) Applicants: AGFA HEALTHCARE NV, Mortsel (BE); VRVis Forschungs GmbH, Vienna (AT); AVL LIST GMBH, Graz (AT); IMP FORSCHUNGSINSTITUT FUR MOLEKULARE PATHOLOGIE GMBH, Vienna (AT)

(72) Inventors: David Major, Mortsel (BE); Jiri Hladuvka, Mortsel (BE); Katja Buhler, Mortsel (BE); Florian Schulze, Mortsel (BE)

(73) Assignees: AGFA HEALTHCARE NV, Mortsel (BE); VRVIS FORSCHUNGS GMBH, Vienna (AT); IMP FORSCHUNGSINSTITUT FUR MOLEKULARE PATHOLOGIE GMBH, Vienna (AT)

( * ) Notice: Subject to any disclaimer, the term of this patent is extended or adjusted under 35 U.S.C. 154(b) by 0 days.

(21) Appl. No.: 14/416,711

(22) PCT Filed: Jul. 23, 2013

(86) PCT No.: PCT/EP2013/065457
§ 371 (c)(1),
(2) Date: Jan. 23, 2015

(87) PCT Pub. No.: WO2014/016268
PCT Pub. Date: Jan. 30, 2014

(65) Prior Publication Data
US 2015/0173701 A1    Jun. 25, 2015

Related U.S. Application Data

(60) Provisional application No. 61/678,108, filed on Aug. 1, 2012.

(30) Foreign Application Priority Data

Jul. 24, 2012  (EP) ..................................... 12177656

(51) Int. Cl.
*G06K 9/00* (2006.01)
*A61B 6/00* (2006.01)
(Continued)

(52) U.S. Cl.
CPC ............... *A61B 6/468* (2013.01); *A61B 5/4566* (2013.01); *A61B 6/032* (2013.01); *A61B 6/5217* (2013.01);
(Continued)

(58) Field of Classification Search
CPC ...... A61B 6/505; A61B 6/5217; A61B 6/468; A61B 6/032; A61B 5/4566; A61B 2560/0295; G06T 2207/30012; G06T 7/0081; G06T 7/0087; G06T 2207/10081; G06T 7/0097; G06K 9/6297
USPC .......................................................... 382/131
See application file for complete search history.

(56) References Cited

U.S. PATENT DOCUMENTS

2011/0064291 A1    3/2011 Kelm et al.

OTHER PUBLICATIONS

Roberts et al., "Automatic Segmentation of Lumbar Vertebrae on Digitised Radiographs Using Linked Active Appearance Models," Proceedings of Medical Image Understanding and Analysis, vol. 1, Jan. 1, 2006, pp. 120-124.*
Official Communication issued in International Patent Application No. PCT/EP2013/065457, mailed on Oct. 8, 2013.
(Continued)

*Primary Examiner* — Gregory F Cunningham
(74) *Attorney, Agent, or Firm* — Keating & Bennett, LLP (57) ABSTRACT

A method, an apparatus, and a system label one or more parts of a spine in an image, in particular a computed tomography (CT) image, of a human or animal body, and in order to achieve a reliable spine labeling and a high throughput of images, match a model of a spine segment with segments of the spine in the image by starting matching the model of a spine segment with an initial segment of the spine in the image, wherein the initial segment of the spine in the image is located at an initial position along the spine in the image, and continue to match the model of a spine segment with one or more further segments of the spine in the image, wherein the further segments of the spine in the image are located at positions farther along the spine in the image.

15 Claims, 4 Drawing Sheets

(51) Int. Cl.
  *G06T 7/00* (2006.01)
  *A61B 5/00* (2006.01)
  *A61B 6/03* (2006.01)
  *G06K 9/62* (2006.01)

(52) U.S. Cl.
  CPC ............ *G06K 9/6297* (2013.01); *G06T 7/0081* (2013.01); *G06T 7/0087* (2013.01); *G06T 7/0097* (2013.01); *A61B 6/505* (2013.01); *A61B 2560/0295* (2013.01); *G06T 2207/10081* (2013.01); *G06T 2207/30012* (2013.01)

(56) References Cited

OTHER PUBLICATIONS

Roberts, "Automatic Detection and Classification of Vertebral Fracture Using Statistical Models of Appearance," http://personalpages.manchester.ac.uk/staff/martin.roberts/mrthesis.pdf, downloaded Jan. 1, 2008, pp. 1-205.

Major, "Markov Random Field Based Structure Localisation of Vertebrae for 3D-Segmentation of the Spine in CT Volume Data," http://www.cg.tuwien.ac.at/researc/publications/2010/major-2010-mrf/major-2010-mrf-paper.pdf, downloaded May 11, 2010, 102 pages.

\* cited by examiner

METHOD, APPARATUS AND SYSTEM FOR AUTOMATED SPINE LABELING

CROSS-REFERENCE TO RELATED APPLICATIONS

This application is a 371 National Stage Application of PCT/EP2013/065457, filed Jul. 23, 2013. This application claims the benefit of U.S. Provisional Application No. 61/678,108, filed Aug. 1, 2012, which is incorporated by reference herein in its entirety. In addition, this application claims the benefit of European Application No. 12177656.1, filed Jul. 24, 2012, which is also incorporated by reference herein in its entirety.

BACKGROUND OF THE INVENTION

1. Field of the Invention

The present invention relates to a method and a corresponding apparatus and system for automated labeling of a spine in an image, in particular a computed tomography (CT) image, of a human or animal body.

2. Description of the Related Art

The acquisition of CT images with and without contrast agent of abdomen, thorax and/or neck is a routine procedure for the diagnosis of a multitude of diseases or injuries. The spinal column represents a natural reference structure of the upper part of the body for describing the locations of organs and pathologies. To be used as a reference system in daily clinical routine, the vertebrae and/or intervertebral disks in the image have to be labeled. A manual labeling can be time consuming, especially if only arbitrary parts of the spine are visible in the data. Therefore, automatic approaches are of interest which deliver labeling results after image acquisition without any user interaction.

For the labeling task, a sparse localization of spine components, e.g. vertebrae and/or disks, is sufficient. Within this context, the term "sparse" refers to the requirement according to which correct anatomical labels should be visible in all views showing a certain vertebra or intervertebral disk, and optionally also in a 3D rendering. This does not necessarily require a full segmentation of all spinal structures. The localization of centers of disks and vertebrae and a coarse approximation of their extent delivers adequate results.

Although this task seems to be trivial, the realization of a fully automatic labeling system for 3D CT data supporting radiologists is challenging: The labeling should be available within a reasonable time in order to guarantee a fast diagnosis after image acquisition. Nonetheless, the labeling algorithm has to reliably handle varying resolution and image quality, showing spinal columns with variations in size, shape, bone densities and varying number of vertebrae. Presence of contrast agent or pathologies like scoliosis, collapsed disks, broken vertebrae, degenerative changes or fused vertebrae based on surgical procedures make high demands on the flexibility of the chosen methods.

SUMMARY OF THE INVENTION

Preferred embodiments of the invention provide a method, apparatus and system for automated labeling of a spine in an image of a human or animal body with high reliability and high image throughput.

The advantages and benefits of the preferred embodiments are achieved by the method, apparatus and system as defined below.

The method according to a preferred embodiment of the invention comprises the following steps: a) matching a model of a spine segment with segments of the spine in the image by starting matching said model of a spine segment with an initial segment of the spine in the image, wherein said initial segment of the spine in the image being located at an initial position along the spine in the image, and by continuing matching said model of a spine segment with one or more further segments of the spine in the image, wherein said further segments of the spine in the image being located at further positions along the spine in the image, wherein said model of a spine segment relates to anatomical properties of one or more parts of a spine, and b) labeling one or more parts of the spine in the image in response to step a).

The apparatus according to preferred embodiment of the invention comprises an image processing unit for executing and/or controlling the following steps: a) matching a model of a spine segment with segments of the spine in the image by starting matching said model of a spine segment with an initial segment of the spine in the image, wherein said initial segment of the spine in the image being located at an initial position along the spine in the image, and by continuing matching said model of a spine segment with one or more further segments of the spine in the image, wherein said further segments of the spine in the image being located at further positions along the spine in the image, wherein said model of a spine segment relates to anatomical properties of one or more parts of a spine, and b) labeling one or more parts of the spine in the image in response to step a).

The system according to preferred embodiment of the invention comprises an image acquisition unit, in particular a computed tomography (CT) unit, for acquiring at least one image of at least a part of a human or animal body and an apparatus for automated labeling of a spine in an image.

The preferred embodiments of the invention include a fully automatic algorithm for labeling arbitrary parts of the vertebral column shown in CT data. The algorithm finds an initial position with its anatomical label by detection of reference regions (e.g. sacrum) and subsequently labels all remaining visible disks and vertebrae automatically. Preferably, a high-performance method for sparse structure localization by Markov Random Fields (MRF) is applied, wherein sparse 3-disk MRF models are built and, starting from the initial position, propagated to all parts of the spine. Preferably, a boosted decision tree based feature detection method inside regions of interest is used for optimization of the MRF model matching. Moreover, prior knowledge on spine anatomy and appearance is considered.

Due to the preferred embodiments of the invention, high precision results—even for CT scans of only few vertebrae—are obtained in less time so that both high reliability and high throughput of images to be labeled are achieved. E.g., for volume images constructed from 512×512 axial slices an average labeling precision of 99.0% in about 2 minutes is achieved.

In the context of the invention, the term "part of a spine" preferably relates to a vertebra or intervertebral disk of a spine. The terms "spine segment" and "segment of a spine" preferably relate to a portion of a spine comprising one or more parts of the spine, in particular one or more vertebrae and/or intervertebral disks. Accordingly, an "initial segment of the spine" or a "further segment of the spine" comprises one or more parts of the spine located at an initial or a further position, respectively, on or along the spine.

The term "matching" or "to match" in the sense of the invention relates to a comparison of said model of a spine segment with segments of the spine in the image and/or an examination whether the model of a spine segment corresponds and/or correlates with segments of the spine in the image.

Further, the term "in response to" relating to matching the model of a spine segment with segments of the spine in the images means that one or more parts of the spine are labeled dependent on and/or subject to the result of the mentioned comparison and/or examination step. In particular, if a model of a spine segment corresponds and/or correlates with a segment of the spine in the image, one or more parts, i.e. vertebrae and/or disks, of said segment of the spine in the image are labeled according to the corresponding parts of the model of a spine segment.

In a preferred embodiment of the invention, said further positions correspond to positions propagating from said initial position. This means that upon completion of matching said model of a spine segment with said initial segment of the spine in the image, said model of a spine segment is matched with at least one first further segment of the spine being located at a first further position, wherein said first further position being next to said initial position and/or said first further segment of the spine being adjacent to said initial segment of the spine. Further, upon completion of matching said model of a spine segment with said first further segment of the spine in the image, said model of a spine segment is matched with at least one second further segment of the spine being located at a second further position, wherein said further position being next to said first further position and/or said second further segment of the spine being adjacent to said first further segment of the spine. This matching process may be repeated for third, fourth, fifth etc. further segments of the spine in the image being located at respective further positions. By matching the spine model with propagating positions and respective segments of the spine, only one promising initial position has to be established making the inventive approach very fast and reliable.

In another preferred embodiment of the invention, one or more parts of the spine in the image correspond to one or more vertebrae and/or intervertebral discs of the spine in the image. By this, highly relevant and recognizable parts of the spine can be labeled very quickly.

According to a further preferred embodiment, said model of a spine segment relates to anatomical properties of two to five vertebrae and/or intervertebral discs of a spine. In particular, said model of a spine segment relates to anatomical properties of three intervertebral discs of a spine and/or to anatomical properties of two vertebrae of a spine. As a result, only relatively small segments of the spine in the image comprising a small number of vertebrae and/or intervertebral discs are sufficient in order to ensure high reliability and throughput.

Preferably, said three intervertebral discs of the spine are associated with said two vertebrae of the spine. In this context, the term "associated" means that said model of a spine segment considers anatomical properties of two consecutive vertebrae, a disk between these two consecutive vertebrae and two disks adjacent to—i.e. at the "bottom" and "top" of—these two consecutive vertebrae. This type of spine segment model results both in a considerable increase of image throughput in daily routine and a high reliability in spine labeling. Because only small segments of the spine are required without adverse effects on the reliability, the flexibility and versatility of the invention is further enhanced.

According to another preferred embodiment of the invention, said initial position of a segment of the spine in the image is established by considering anatomical knowledge about a spine. Preferably, said initial position of an initial segment of the spine in the image is established by detecting at least one anatomical landmark of the spine in the image. In particular, said at least one anatomical landmark relates to one of: a vertebra (T1) at a first rib, a vertebra (T12) of a last rib and/or a sacral foramina (S1). In this way, a reliable and promising initial position leading to good matching results is established very quickly so that image throughput and labeling reliability are still increased.

Preferably, before establishing an initial position of an initial segment, the spinal canal of the spine is detected. Subsequently, one or more initial segment candidates, in particular intervertebral disks, being located next to the spinal canal are determined. Moreover, so-called transition detectors relating to transition disks, e.g. C7/T1, T12/L1 or L5/S1, are determined.

Within the context of the invention, the term "detector" or "feature detector" refers to methods that aim at computing abstractions of image information and making local decisions at every image point whether there is an image feature, e.g. in particular an interesting part of the image, of a given type at that point or not. Accordingly, the term "transition detector" refers to a method for finding a transition between at least two image features.

Moreover, it is preferred that said initial position of a segment of the spine in the image is established by disk appearance profiles or disk profiles, in particular by profiles of the intervertebral disk candidates and/or the transition detectors. Preferably, a disk label is assigned to the most prominent disk candidate.

In a further preferred embodiment of the invention, said initial position of a segment of the spine in the image is established by deducing an initialization disk by regular expression matching, i.e. by matching the disk profile to a full-spine profile. The term "regular expression matching" in the context of the invention relates to a regular expression which provides a concise and flexible way to match, i.e. to specify and recognize, patterns, e.g. strings or character patterns of a text or patterns or profiles of an image or a part thereof.

Preferably, a disk profile corresponds to a string ("TT-T.LLL.") of region classes to which a set of disk candidates ($\{\theta_m\}$) is mapped by classifying each disk candidate ($\theta_m$) to a region class ("C", "T", "L") or region transition uncertainty (".").

Preferably, a set of disk candidates ($\{\theta_m\}$) is detected by disk detectors ($\Phi_C$, $\Phi_T$, $\Phi_L$) which are trained to detect disks in the cervical ("C"), thorax ("T") and lumbar areas ("L") of the spine, respectively.

Preferably, said initial position of a segment of the spine in the image is established by deducing an initialization disk by regular expression matching, wherein a disk profile ("TT-T.LLL.") is matched to a full-spine profile ("CCCCCCTTTTTTTTTTTLLLLL").

Preferably, multiple initialization disk candidates can result from the region transition uncertainty (".") in the disk profile ("TTT.LLL."). Preferably, multiple initialization disk candidates are resolved by multiple labeling runs.

Preferably, said initial position of a segment of the spine in the image is established by deducing an initialization disk by localizing one of three most distinguishing transition disks (C7/T1, T12/L1, L5/S1) of the spine.

Preferably, transition disks (C7/T1, T12/L1, L5/S1) are detected by transition detectors ($\Phi_{CT}$, $\Phi_{TL}$, $\Phi_{LS}$) which are trained to detect cervical/thorax (CT), thorax/lumbar (TL) and lumbar/sacrum (LS) transitions.

Preferably, said initial position of a segment of the spine in the image is established by considering Markov Random Field (MRF) matching qualities. A MRF in the context of the invention is a graphical model of a joint probability distribution. It consists of an undirected graph in which the nodes represent random variables. A MRF is a convenient and consistent way to model context-dependent entities such as image pixels and correlated features. This is achieved by characterizing mutual influences among such entities using conditional MRF distributions.

The preferred steps, alone or in combination, set forth above also contribute to a further enhancement of reliability and image throughput.

Further advantages, features and examples of the present invention will be apparent from the following description of following figures:

DETAILED DESCRIPTION OF THE PREFERRED EMBODIMENTS

Figure 1:
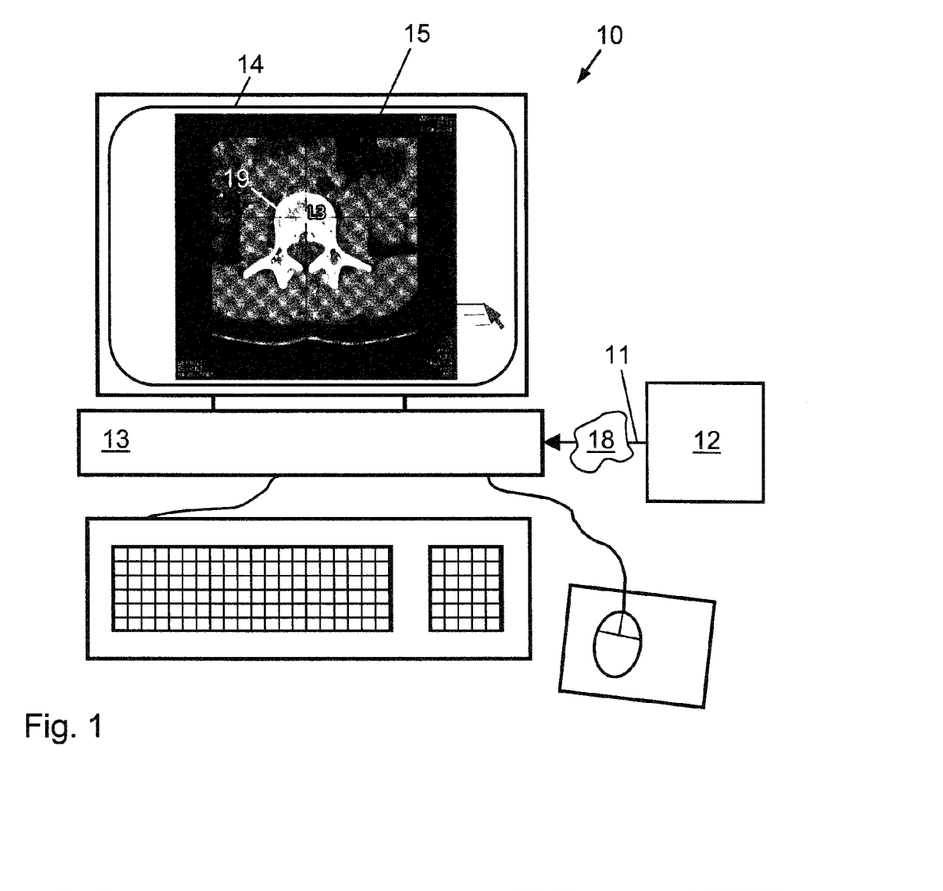
FIG. 1 shows an example of an apparatus and a system according to a preferred embodiment of the invention.

FIG. 1 shows an example of an apparatus 10 and a system according to a preferred embodiment of the invention. A medical image data set 11 comprising a plurality of images, in particular slice images, of a human or animal body is acquired by a medical imaging apparatus 12, in particular a computer tomography (CT) apparatus.

The apparatus 10 comprises a control unit 13, e.g. a workstation or a personal computer (PC), to which the image data set 11 is fed. Preferably, the image data set 11 can be transferred from the medical imaging apparatus 12 to the control unit 13 via a data network 18 to which the control unit 13 is, at least temporarily, connected. For example, the data network 18 can be a local area network (LAN) or wireless LAN (WLAN) in a hospital environment or the internet.

Preferably, the control unit 13 is configured to generate a volume reconstruction and/or a slice view 15 of the image data set 11 on a display 14, e.g. a TFT screen of the workstation or PC, respectively. Moreover, the control unit 13 is designed to label one or more parts of a spine in the image data set 11 according to preferred embodiments of the invention.

In the example shown in FIG. 1, a vertebra 19 in the axial slice view 15 is labeled, i.e. marked or denoted, with a label "L3" indicating that the displayed vertebra 19 corresponds to the third lumbar vertebra of the spine.

Figure 2:
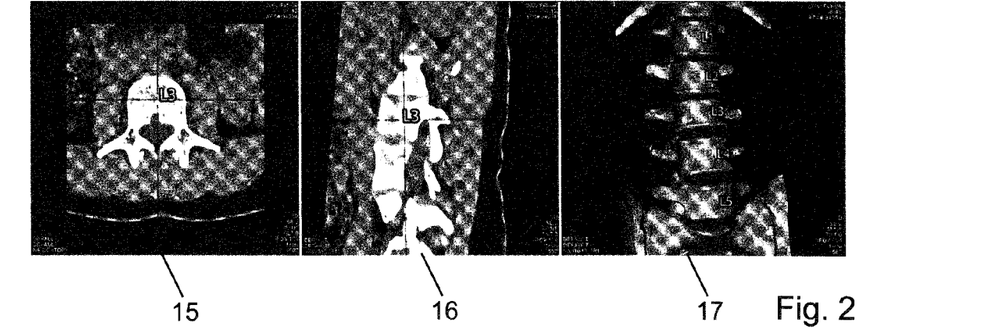
FIG. 2 shows an example of a multi-view rendering of vertebra labels in a radiology software.

FIG. 2 shows an example of a multi-view rendering of vertebra labels in a radiology software. The left part of FIG. 2 again shows the axial slice view 15 rendered on the display 14 shown in FIG. 1. The middle part of FIG. 2 shows a sagittal slice view 16 of a spinal segment, wherein respective vertebra is labeled with "L3". In the right part of FIG. 2 a three-dimensional representation of the image data set is shown, wherein all of the vertebrae contained in the image are labeled with respective labels "L1" to "L5".

The spinal column represents a natural reference frame of the upper part of human body. To localize nearby organs and pathologies, sparse spine labeling is sufficient, wherein correct vertebra/disk labels are visible in arbitrary 2D and 3D views prior their segmentation. According to an aspect of the invention, an automatic, segmentation-free approach to sparsely label spinal columns in 3D CT datasets is proposed and an according framework was designed with two main goals in mind. First, to relax requirements on the input data for labeling of both full and partial spine scans. Though presence of sacrum, T12, or T1 vertebrae in the data is predominantly used, it is not strictly necessary. Second, to be used in daily clinical routines, the method, apparatus and system according to preferred embodiments of the invention need to be high throughput, capable of processing thousands of slices in few minutes. To accomplish these goals, structural knowledge from training data is preferably encoded in probabilistic boosting trees and used to detect relevant landmarks in the incoming scans. Desired disk landmarks and labels are then localized preferably by Markov Fandom Field-based matching of sparse appearance models which encode the anatomical knowledge.

The spine labeling approach outlined above will be presented in more detail in the following.

1. Building Spine-Related Models 1.1. Data Requirements

In contrast to approaches according to the state of the art, a preferred embodiment the invention does not expect any specific part of the spine to be present in a CT scan. Rather, the only requirement is to have at least a three-intervertebral disk part of the spine in the data. Additionally, the following information to be available in the DICOM tags is required: (1) a CT-to-Hounsfield intensity transformation and (2) the patient position.

1.2. Training Data Annotation

Having these requirements met, volumes $I_k$ in Hounsfield scale and in right-handed head-first supine (face-up) orientation of the patient are reconstructed. The data is annotated in the following way: For each disk landmark $d_i$, i=1 ... 23, present in image $I_k \in S$, k=1 ... 48, the center position of the disk $d^k_i$ is annotated with an anatomical label $\Lambda_i \in \{C2/C3, C3/C4, \ldots, L4/L5, L5/S1\}$. A cylinder $K^k_{di}$ approximating the disk is positioned at the disk center $d^k_i$. Furthermore, next to the disk landmarks $d_i$ canal landmarks $c_i$ with anatomical labels $\Lambda_i$ are placed within the spinal canal at position $c^k_i$, lying on the perpendicular defined by the spinal canal and the disk center. The canal landmark set is extended by landmarks defined by the middle point lying on a linear interpolation of $c^k_i$ and $c^k_{i+1}$. Cylinders $K^k_{ci}$ around $c^k_i$ approximate the extent of the spinal canal. Further landmarks $b_j$, j=1 ... 12 with anatomical labels $\theta_j \in \{T1, \ldots, T12\}$ are placed in the middle of rib bodies $b^k_j$ and $s_1$, $s_2$ in the center of the two uppermost sacral foramina $s^k_1$, $s^k_2$. Cylinders $K^k_{bj}$; $K^k_{s1}$, $K^k_{s2}$ were placed around $b^k_j$, $s^k_1$, $s^k_2$ to approximate their extent.

Figure 3:
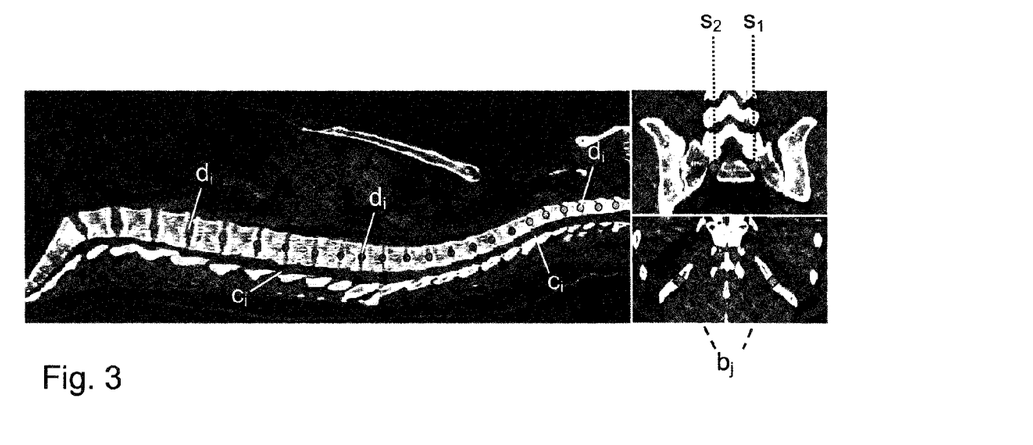
FIG. 3 shows examples of CT images with annotated landmarks.

FIG. 3 shows examples of CT images in a sagittal, coronal and axial plane, respectively, which have been annotated accordingly with landmarks, i.e., disk centers $d_i$, spinal canal centers $c_i$, ribs $b_j$ and sacral foramina centers $s_1$, $s_2$. For a better clarity, the interpolated spinal canal landmarks are not visualized in this representation.

1.3. Learning Appearance of Target Regions

In order to detect and label the intervertebral disks, three detectors dedicated to cervical, thorax, and lumbar disks are trained for this purpose. To prune the input volume and to clean the disk outliers, however, it is started with detecting the most reliable reference structure, i.e. the spinal canal. To deduce an initialization label, three detectors are further trained to detect T1 rib, T12 rib, and the uppermost sacral foramina.

1.3.1. Spinal Canal Detector: $\Phi_S$

Preferably, the spinal canal is chosen as a central part of spine-related problems. Positive samples for the spinal canal detector $\Phi_S$ are generated within the cylinders $K^k_{ci}$ around the annotated points $c^k_i$. Negative samples are generated randomly, constrained to have a minimal distance of 10 mm to positive regions.

1.3.2. Disk Detectors: $\Phi_C, \Phi_T, \Phi_L$

In order to place labels inside the intervertebral disks, three disk detectors $\Phi_C, \Phi_T, \Phi_L$ are learned to detect the disks in the cervical, thorax, and lumbar areas, respectively.

Positive disk samples are generated from the cylindrical disk approximation $K^k_{di}$ of the respective region: $\Phi_C$ is learned from {C2/C3, ..., C7/T1} disks, $\Phi_T$ from {T1/T2, ..., T12/L1}, and $\Phi_L$ from {L1/L2, ..., L5/S1}.

Negative samples are taken from the counterpart disks as well as from random distribution with assured minimal distances of 10 mm to the positive samples.

While the disk detectors best respond in areas they have been trained for, false positive responses may occur frequently especially in the cervical/thorax and thorax/lumbar transitions. The disks can be therefore best localized as clusters in a union $\Phi_C \cup \Phi_T \cup \Phi_L$ of all three disk detector responses.

The association of a mixed disk cluster with a particular region, however, needs to be learned from the relative contributions of the responses $\Phi_C, \Phi_T$ and $\Phi_L$. The posterior probabilities of the three detectors are combined to classify disk clusters into one of the respective regions "C", "T", "L", or "." to reflect region transitions and further uncertainties.

1.3.3. Transition Detectors: $\Phi_{CT}, \Phi_{TL}, \Phi_{LS}$

The following three detectors are trained to detect the three transitions where the labeling can easily be initialized from: cervical/thorax, thorax/lumbar, and lumbar/sacrum. The feature detector $\Phi_{CT}$ is trained to detect voxels in the T1 rib. Positive rib samples are generated within cylindrical regions $K^k_{b1}$ around the rib points $b^k_1$;

$\Phi_{TL}$ is trained to detect voxels in the T12 rib. Similar to T1, positive T12 rib samples are generated within cylinders $K^k_{b12}$ around the rib points $b^k_{12}$;

$\Phi_{LS}$ is trained to detect the sacral foramina points $s^k_1, s^k_2$. Positive samples are constrained to the sacral foramina cylinder approximations $K^k_{s1}, K^k_{s2}$.

As negative samples for all of the transition detectors, all remaining annotated parts, manually selected parts (i.e. transverse processes of vertebrae) of the body and randomly sampled points with a safety margin of 10 mm to the positive samples are taken.

1.3.4. Employing Probabilistic Boosting Trees

To perform the feature detection during both training and testing, probabilistic boosting trees (PBT) are employed. PBTs are special kinds of decision trees which hold an ensemble of weak classifiers at each tree node and compose them into one strong classifier. The weak classifiers preferably used in preferred embodiments of the invention include so-called Haar-like features, image derivatives (intensity, gradient magnitude, structure tensor, and principal curvature) and their histograms.

Preferably, cascading, classifier sorting and a multi-resolution scheme are used in order to optimize time performance. Cascading considers only true samples running along the tree, while classifier sorting uses cheap classifiers at first and more expensive ones at deeper levels of the tree. The multi-resolution scheme significantly reduces the amount of voxels to be processed. Each detector consists of 3 boosted decision tree classifiers $\Phi^n_p$ (n=0 ... 2) for 3 levels of resolution. Input volumes $I_k$ are resampled into a pyramid of 3 isotropic grids $I^n_k$ with voxel sizes of $2^n$ mm. During classification the feature detectors are applied in a coarse-to-fine manner, i.e. $\Phi^2_p \to \Phi^1_p \to \Phi^0_p$, early terminating as soon as any test fails.

1.4. The 3-Disk Model

The feature clouds from disk detectors are usually not suitable for the final result. First, there are false positive (outliers) both outside and inside of the disk column. Second, there are problematic data, e.g. with broken vertebrae collapsed disks, where disks are detected weakly or even remain undetected.

To correct the disk detection afterwards and to compensate for the weak or missing disks feature clouds, sparse MRF appearance models record a priori information about appearance of local image regions, of the edges between them and about the geometrical setup of these regions.

The geometrical setup and the anatomical appearance of a compound of 3 consecutive disks is modeled and adapted according to morphometry while propagating along the spine. This has three advantages over a model of the full spinal column. First, the matching is done locally and is therefore fast and robust. Second, anatomical variation can be easily integrated into the whole framework. Third, the framework is applicable on datasets which contain only parts of the spine.

Figure 4:
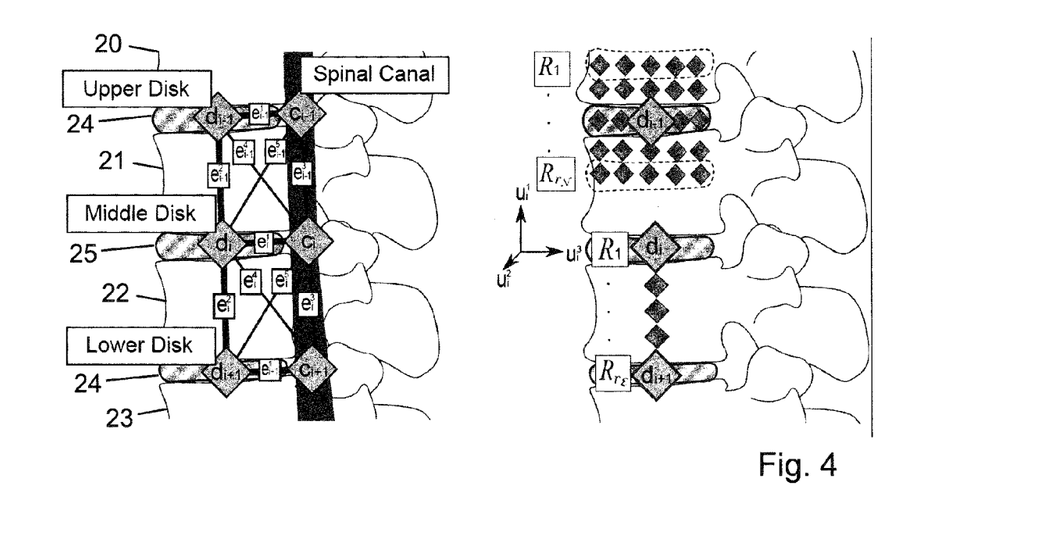
FIG. 4 shows (left) a sparse 3-disk model $\mathcal{M}_i$ for a fixed intervertebral "Middle Disk" $d_1$ and (right) a 2D sagittal projection of a steerable sampling pattern around a disk $d_i$ and along an edge defined by $d_i$ and $d_{i+1}$, wherein pattern layers define regions $R_1 \ldots R_r$.

Left part of FIG. 4 shows vertebrae 20 to 22 and intervertebral disks 24 to 26 of a spine segment. In the model $\mathcal{M}_i$ of a spine segment set forth below, preferably two consecutive vertebrae 21 and 22, a middle disk 25 located between the consecutive vertebrae 21 and 22 as well as an upper and lower disk 24 and 26 adjacent to the upper side of upper vertebra 21 or lower side of lower vertebra 22, respectively, are considered.

1.4.1. Setup

For a fixed disk label $\Lambda_i$, computation of the 3-disk model $\mathcal{M}_i$ involves 6 nodes and preferably 11 or 5 edges around disk landmark $d_1$, over all training images that contain the entire 3-tuple of disks $d_{i-1}, d_i, d_{i+1}$. This is illustrated in left part of FIG. 4, in which the 6 nodes $d_i, d_{i+1}, c_i, c_{i+1}$ and $c_i$ are connected by 11 edges. For computation of the 3-disk model around disk landmark $d_1$ preferably all of the 11 edges are considered or, alternatively, only a 5-edge subset thereof is involved, as exemplarily indicated in FIG. 4 by thick lines.

For each training volume $I_k \in S_{tr}$ a local coordinate frame is spanned with reference point at the i-th disk landmark $d_i$ and three orthogonal vectors:

$$u_i^1 = c_{i-1} - c_{i+1},\ u_i^2 = u_i^1 \times (0,-1,0),\ u_i^3 = u_i^1 \times u_i^2$$

Subsequently, a morphometry feature vector $\mathcal{G}^k_i$ is computed to capture the geometrical configuration of the 6 nodes and appearance feature vectors $\mathcal{N}^k_i, \mathcal{E}^k_i$ to sparsely model the appearance of both the 6 nodes and the 11 or 5 edges, respectively.

In the context of the invention, the term "feature vector" in general relates to a multi-dimensional vector of numerical features that represent an object. Accordingly, a "morphometry feature vector" relates to a multi-dimensional vector of numerical features relating to a quantitative analysis of form, i.e. size and shape, of an object, and an "appearance feature vector" relates to a multi-dimensional vector of numerical features relating to a quantitative analysis of the texture, in particular the surface texture, of an object.

The model $\mathcal{M}_i$ will be finally computed as an average feature vector across the training data.

1.4.2. The Morphometry Feature Vector

For each edge e its length $\|e\|$ and 3 angles to the local coordinate frame, i.e.

$$\angle eu_i^1, \angle eu_i^2, \angle eu_i^3$$

are computed yielding a 44-dimensional or 20-dimensional feature vector, respectively:

$$\mathcal{G}_i^k = \{\|e\|, \angle eu_i^1, \angle eu_i^2, \angle eu_i^3 | e \in \{e_{i-1}^1, \ldots, e_{i-1}^5, e_i^1, \ldots, e_i^5, e_{i+1}^1\}\}$$

1.4.3. Appearance Feature Vectors

The appearance of edges and nodes is modeled by intensity differences between r sampling patterns $R_1, R_2, \ldots, R_r$.

While the edges are sampled linearly, the node sampling patterns are steerable features: layers orthogonal to $u_i^1$ are displaced and scaled according to the captured morphometry. This is illustrated by means of FIG. 4 (right part) showing a 2D sagittal projection of steerable sampling Regions R around the disk $d_{i-1}$ and samples along an edge defined by $d_i$ and $d_{i+1}$, wherein pattern layers define the regions $R_1 \ldots R_{rN}$ or $R_{re}$, respectively. $u_i^1, u_i^2$ and $u_i^3$ define the local coordinate frame at disk $d_i$.

For each node/edge a feature vector D is created computing intensity sum differences between all possible combinations of region pairs $R_A$ and $R_B$:

$$D = \left[ \sum_{p \in R_A} I(p) - \sum_{q \in R_B} I(q) \right]_{\left( \begin{array}{l} A=1\ldots r \\ B=A+1\ldots r \end{array} \right)}$$

This yields $$\binom{r}{2}\text{-dimensional}$$

appearance vectors for each edge and the 6 nodes. The edge appearance can be excluded by setting rN=0. Depending on an actual configuration, the edge appearance vector $\mathcal{E}_i^k$ becomes thus $$11 \times \binom{r\varepsilon}{2}\text{-dimensional}$$

$$5 \times \binom{r\varepsilon}{2}\text{-dimensional}$$

or 0-dimensional, respectively, and the nodes appearance vector $$\mathcal{N}_i^k \; 6 \times \binom{rN}{2}\text{-dimensional}$$

1.4.4. The Model

The final edge-node feature vector of model $\mathcal{M}_i$ is computed by averaging the feature vectors of all training data, $S_{tr}$:

$$\mathcal{M}_i = (\overline{\mathcal{G}}_i, \overline{\varepsilon}_i, \overline{\mathcal{N}}_i) = \frac{1}{|S_{tr}|} \sum_{I_k \in S_{tr}} \left( \overbrace{\mathcal{G}_i^k, \varepsilon_i^k}^{edges}, \overbrace{\mathcal{N}_i^k}^{nodes} \right) \quad (1)$$

Models $\mathcal{M}_i$ are built for every disk label from C3/C4 to L4/L5, i.e., $2 \leq i \leq 22$.

In addition, the models $\mathcal{M}_{20}, \mathcal{M}_{21}, \mathcal{M}_{22}$ are associated with mean distances $s^-_{21}, s^-_{22}, s^-_{23}$, of their bottommost disks centers, $d_{21}; d_{22}; d_{23}$, to the sacral foramina.

2. Labeling Framework

In this section, the spine auto-labeling framework following its components will be described with reference to FIG. 5 which shows a sagittal projection of a segment of a spine in an image at different phases or steps (corresponding to part a to f of FIG. 5) of the method according to a preferred embodiment of the invention. In the given example, the segment of the spine in the image comprises 13 vertebrae and 14 intervertebral disks.

After input of CT image data (FIG. 5a), feature detection is performed in order to prune the search space for the subsequent model matching. Here, a detection of the spinal canal (see FIG. 5b and sec. 2.1 below) is followed by a detection of intervertebral disk candidates next to it and by transition detectors (see FIG. 5c and sec. 2.2 below).

A subsequent initialization disk identification is based on the disk candidates, their profile, and on the transition detectors. As a result, a disk label is assigned to the most prominent disk candidate (see FIG. 5d and sec. 2.3 below).

In a following step, model matching and propagation is performed, wherein a 3-disk model, which is determined by the initialization label, is matched to a subset of disk and canal features (see FIG. 5e and sec. 2.4 below). The matching is propagated up and/or downwards until stopping criteria are met (see sec. 2.5 below). In a final step, the CT image of the spine is labeled with respective labels according to the results of the previous model matching and propagation step (see FIG. 5f).

The above-mentioned steps of the spine auto-labeling framework will be described in more detail in the following.

2.1. Spinal Canal

In a preferred embodiment of the invention, the algorithm considers the spinal canal which is a significant feature. Accordingly, the spinal canal feature detector $\Phi_S$ is applied inside the whole volume. Positively classified voxels yield a point cloud. To avoid false positives, a B-spline is fitted to the tallest connected component of this cloud. In the following the B-spline will also be referred to as canal spline ç (see FIG. 5b).

2.2. Disk Candidates and Profile

To accelerate the detection of disk candidates the disk detectors $\Phi_C, \Phi_T, \Phi_L$ are restricted to a region extruded by the largest possible disk along the canal spline ç.

Positively classified voxels yield cervical, thoracic, and lumbar feature clouds, C, T, and L. In order to eliminate false positives and to yield only true disk points, places of highest concentrations of disk points along the canal spline are determined.

The canal spline is sampled at a fixed arc length of 1 mm yielding a set of points and tangents $\{\varsigma_s, \varsigma'_s\}$. Each spline sample ç S is associated with disk feature subsets $C_s$, $T_s$, and $L_s$ less distant than 0.5 mm from a plane defined by $(\varsigma_s, \varsigma'_s)$ and counted: $\Sigma_s = |C_s| + |T_s| + |L_s|$. Canal samples $\varsigma_m$ where $\Sigma_m$ attains local maxima (with respect to a window of the smallest vertebra height) lie in disk planes and the centroids of the corresponding feature clusters $\theta_m = avg(C_m \cup T_m \text{ Å} L_m)$ are picked as disk candidates. The corresponding counts $|C_m| + |T_m| + |L_m|$ are used to classify each disk candidate $\theta_m$ in accordance with section 1.3.2 above, i.e. to a region class "C", "T", "L", or region transition uncertainty ".". The set of all disk candidates $\{\theta_m\}$ is mapped to a string of region classes and is referred to as the disk profile. For example, a disk profile "TTT.LLL." corresponds to a thoracic-lumbar transition with two uncertain disk candidates $\theta_4$ and $\theta_8$. In FIG. 5c, disk detectors $\Phi_T$, $\Phi_L$ and a transition detector $\Phi_{TL}$ are shown.

2.3. Initialization Disk and its Label

From a set of disk candidates $\{\theta_m\}$ an initial one, $\theta_i$, is picked for which a disk label $\Lambda_i$ can be assigned reliably. Preferably, one of the three most distinguishable transition disks C7/T1, T12/L1, and L5/S1 is localized (see sec. 2.3.1 below). If none of these transition disks can be localized, the initialization disk label is deduced by a regular expressions match of the disk profile to a full-spine profile (see sec. 2.3.2 below).

2.3.1. Applying Transition Detectors

The three transition detectors introduced in section 1.3.3 above are applied near the spinal canal if the disk profile suggests it, terminating as soon as the initialization disk can be deduced as follows:

- C7/T1 rib features ($\Phi_{CT}$) are computed next to a potential C-to-T transition. An overlap of the feature points with disk candidates is evaluated in the sagittal projection. The disk candidate with a maximum feature overlap is assigned the disk label C7/T1.
- T12/L1 rib features ($\Phi_{TL}$) are computed next to a potential T-to-L transition. Similar to the former case, the disk candidate with the maximum feature overlap is assigned the disk label T12/L1.
- Sacrum features ($\Phi_{LS}$) are computed in the vicinity of the bottom tip of the spline provided there is a chain of L-class disk candidates at the bottom of the profile. The distance between the centroid of $\Phi_{LS}$ and the bottommost disk candidate is compared to all three disk-to-foramina distances $s^-_{22}$, $s^-_{22}$, $s^-_{23}$ introduced in section 1.4.4. In most of the cases $s^-_{23}$ determines the best match to the transition label L5/S1. For troublesome cases where bottommost disks were undetected the matches to $s^-_{22}$ or even $s^-_{22}$ may decide on the bottommost label, i.e. L4/L5 or L3/L4.

2.3.2. Resolving Ambiguities

If all above transition detectors fail due to insufficient features or lacking features-to-profile correspondence, a regular expression search is applied to match the disk profile to a full-spine profile "CCCCCCTTTTTTTTTTTTLLLLL".

While such a match can happen to be unique, the algorithm has to be prepared to handle eventual multiple candidates resulting from missing transition (e.g. if only a part of thorax in the CT scan is seen) or uncertainties in the disk profile. The example disk profile "TTT.LLL." would yield two matches, "TTTLLLLL" and "TTTLLLLL", with two candidates for label T12/L1, i.e. $\theta_3$ and $\theta_4$. Similarly, "LLL" profile would yield three candidate configurations in the lumbar part, "TTTTTT" would yield 7 candidate configurations in the thorax, and so forth.

Multiple candidates are resolved by multiple labeling runs initialized from each disk-label pair. The labeling results are assessed by MRF matching qualities as shown below.

2.4. Model Matching Using MRFs

Having found the initialization $(\theta_i, \Lambda_i)$ at disk i, the 6-tuple $$(\Theta_{i-1}, \zeta_{i-1}, \Theta_i, \Theta_{i+1}, \zeta_{i+1})$$

of previously identified adjacent disk candidates and their associated canal points become subject to be refined with model $\mathcal{M}_i$ and/or compensated for eventual missing disk features.

A cloud of 100 closest disk or canal features, respectively, is associated to every of the 6-tuple points (see FIG. 4). The 6×100 points become the refinement candidates. The task is to find an optimal match of the model $\mathcal{M}_i$ to one of the $100^6$ possible configurations $\tau_i$ as each of the 6 model nodes attempts to find an optimal position among its 100 associated candidates.

The fitness $$Q(\tau_i | M_i) \tag{2}$$

Q of model $\mathcal{M}_i$ to a particular 6-tuple configuration $\tau_i$ will be assessed by Euclidean distance between the feature descriptor $$(\mathcal{G}_i, \overline{E}_i, \overline{N}_i)$$

of the model (eq. (1)) and a descriptor $$(\mathcal{G}_{\tau i}, E_{\tau i}, N_{\tau i})$$

computed analogically from the configuration $\tau_i$.

As the exact optimal match of the model, i.e. the maximum quality configuration $$\tau_i^* = \underset{\tau_i}{\operatorname{argmax}} Q(\tau_i | \mathcal{M}_i) \tag{3}$$

is NP-hard to find, an efficient approximation approach is applied which involves computation of a $11 \times 100^2$ edge quality matrix E and of a 6×100 node quality matrix C which are fed to a so-called Max-Sum solver.

The reference node $d_i$ of the optimally matched model is fixed as the final position $d^*_i$ associated with the $\Lambda_i$. If the uppermost or bottommost model $\mathcal{M}_2$ or $\mathcal{M}_{22}$, respectively, has been matched, the reference node $d_1$ or $d_{23}$, respectively, of the model is additionally taken as the final position associated with label $\Lambda_1$ or $\Lambda_{23}$, respectively.

Compensating Missing Disks

Insufficient disk features (e.g., due to vertebra collapses, pathologies) would lead to an improper MRF-based match of the model $\mathcal{M}_i$. To account for that, dummy edge and node qualities can be pre-computed from the training data yielding extended quality matrices, a $11 \times (100+1)^2$ matrix E' and a $6 \times (100+1)$ matrix C'. If the model happens to find the optimum using dummy qualities, an extra point is inserted into the set of the disk candidates $\{\theta_m\}$.

2.5. Propagation

After the initial MRF model $\mathcal{M}_i$ has been matched, the algorithm propagates downwards and/or upwards along the canal spline in order to refine the remaining label positions $\{j\}$ in the input volume.

During the downward propagation, $(\theta_{i+1}, \Lambda_{i+1})$ becomes the initialization position/label pair and the 6-tuple $$*(d_i, \zeta_i, \Theta_{i+1}, \zeta_{i+1}, \Theta_{i+2}, \zeta_{i+2})$$

is subject to be refined by the model $\mathcal{M}_{i+1}$. The downward propagation terminates when either of the following criteria is met: the volume data bottom is reached or a marginal disk (L5/S1) is labeled. Upward propagation is analogical to the downward propagation.

The total labeling after upper/downer propagation can be assessed by geometry components of the optimal matches (see eqn. (3)) of models $\{\mathcal{M}_j\}$ to all detected disks $\{j\}$ in the input dataset, excluding models optimized due to a dummy case:

$$Q^\dagger = -\frac{1}{|\{\mathcal{G}_{\tau_j^*}\}|}\sum_j \|\mathcal{G}_{\tau_j^*} - \mathcal{G}_j\| \quad (4)$$

2.6. Finalization

Assessing Multiple Initializations: Labeling results from eventual multiple initializations (section 2.3.2) are compared by total labeling qualities (see eqn. (4)). Labeling with the maximal total labeling quality $Q\uparrow$ becomes the final one.

Vertebra Labels by Interpolation: The model matching framework delivers positions of intervertebral disks. Vertebral body positions and labels are obtained by linear interpolation between adjacent disks.

2.7 Results

Figure 5:
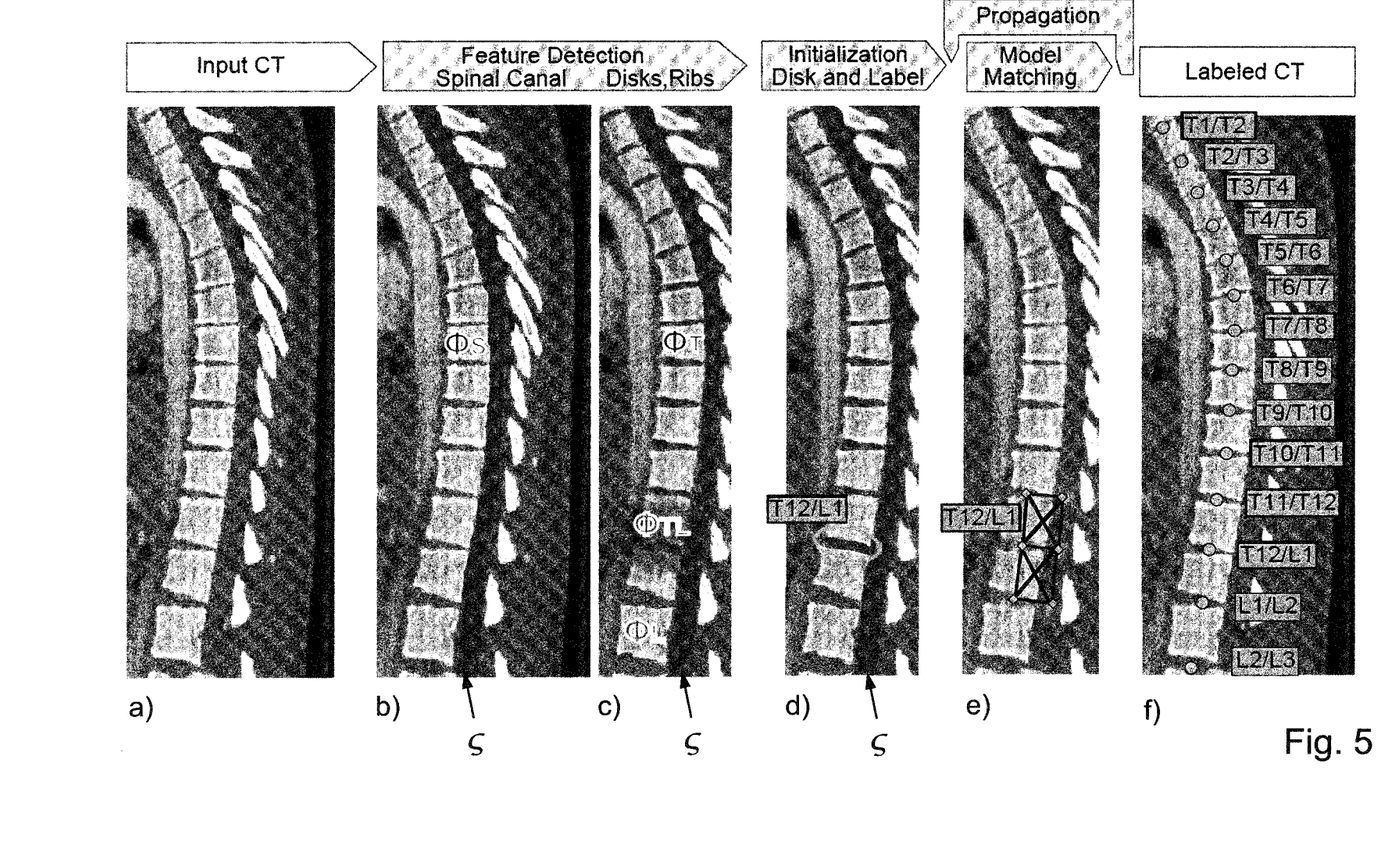
FIG. 5 shows an overview on the spine labeling framework in a sagittal projection.

By applying the method set forth above to the example given in FIG. 5, the intervertebral disk T12/L1 in the spine image is determined as an initialization disk, i.e. an initial segment, of the spine and is labeled accordingly with "T12/L1" (see FIG. 5d).

Subsequently, as shown in FIG. 5e, model matching starts with a model of a spine segment considering properties of three intervertebral disks and two vertebrae around the initialization disk T12/L1 corresponding to the middle disk 25 shown in left part of FIG. 4.

After repetitive propagation of model matching to further segments of the spine, intervertebral disks from L2/L3 to T1/T2 were detected and accordingly labeled in the image as shown in FIG. 5f.

Figure 6:
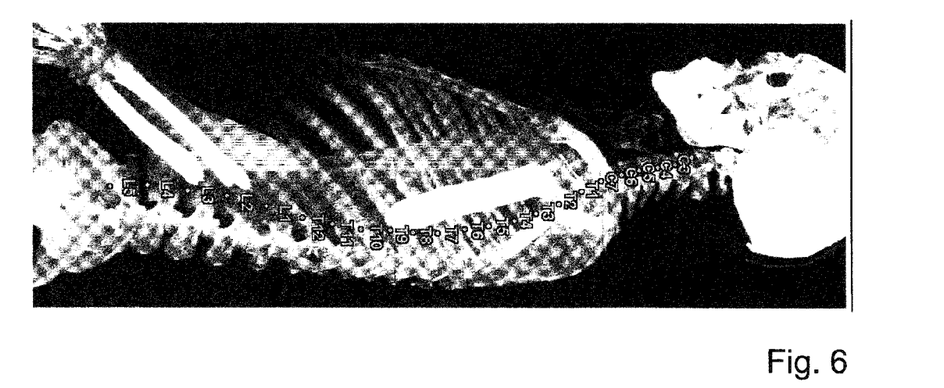
FIG. 6 shows an example of a correctly labeled full-spine dataset.

FIG. 6 shows an example of a full-spine image dataset which has been correctly labeled by a method according to a preferred embodiment of the present invention. As apparent from the figure, the vertebrae represented in the image are annotated with respective spine labels Cn, Tn and Ln from cervical vertebra C3 to lumbar vertebra L5.

Figure 7:
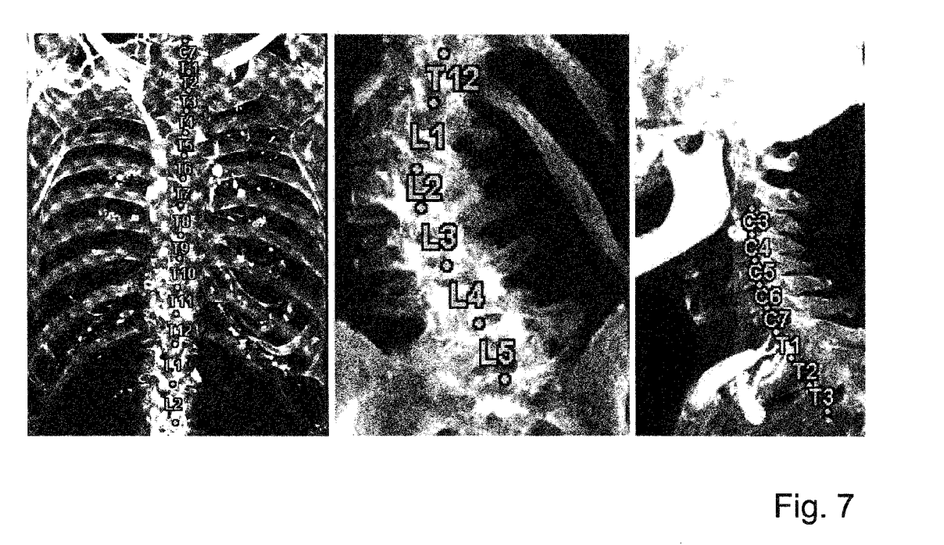
FIG. 7 shows further examples of correctly labeled datasets of parts of a spine.

FIG. 7 shows further examples of labeled image datasets of parts of a spine. The segment of the spine represented in the left image features collapsed vertebrae and herniated disks; despite these unfavorable anatomical conditions, due to preferred embodiments of the invention respective vertebrae are correctly labeled from cervical vertebra C7 to lumbar vertebra L2. Same applies to the middle image featuring an extremely scoliotic spine segment, where the vertebrae are correctly labeled from thoracic vertebra T12 to lumbar vertebra L5. The right image shows a correctly labeled cervical image data set, labeled from C3 to T3.

3. Conclusion

In summary, by the method, apparatus and system disclosed herein both full and partial CT scans of a spine get labeled reliably and in a clinically reasonable time. With a recall of 95.5% the algorithm set forth above automatically labels a broad spectrum of input volumes including full spinal columns, partial scans at different regions (cervical, thorax, lumbar), data with pathologies (e.g., scoliosis, osteoporosis, disk collapses), as well as data acquired by different vendors (like GE, Philips or Siemens) at a variety of spatial resolutions. An exemplary 512×512×5966 dataset labeled in 5.7 minutes evidences that the method scales very well.

To cope with all this variance in the input data, a framework was introduced based on following ideas: First, fast feature detection of target structures, mainly intervertebral disks and spinal canal, is refined by three-disk models. Second, a correct labeling is assured by learned structures to identify the initial disk at one of C7/T1, T12/L1, and L5/S1.

Preferably, the framework set forth above can be extended by disk orientation estimation. This can reliably be derived from the canal spline tangent. In fact, the canal features and spline fitting of our framework are robust so that it is also possible to investigate the Frenet frame (i.e., curvature and torsion) of the canal spline to quantify spine abnormalities.

Moreover, it is assumed within the algorithm set forth above that a standard atlas of the spinal column with 24 vertebrae, thought anomalies with one more or less vertebra exists. Such cases can be resolved by looking at the number of disk candidates relative to the reference structures (ribs, sacral foramina) in the disk initialization step. Furthermore, it is possible to train the fully automatic spine labeling framework on MR data and to extend the training data by more examples which cover a higher degree of anomalies and deviations in morphometry, e.g., spine scans from children.

The invention claimed is:

1. A method for labeling one or more portions of a spine in an image of a human or animal body, the method comprising the steps of:
   a) matching a model of a spine segment with segments of the spine in the image by:
      starting matching the model of the spine segment with an initial segment of the spine in the image, wherein the initial segment of the spine in the image is located at an initial position along the spine in the image; and
      continuing matching the model of the spine segment with one or more further segments of the spine in the image, wherein the one or more further segments of the spine in the image are located at farther positions along the spine in the image, and the model of the spine segment relates to anatomical properties of one or more portions of the spine; and
   b) labeling the one or more portions of the spine in the image in response to step a); wherein
   an initial position of an initialization disk of the spine in the image is established by a disk profile corresponding to a string of region classes to which a set of disk candidates is mapped by classifying each disk candidate of the set of disk candidates to a region class or a region transition uncertainty; and
   the disk profile is matched to a full spine profile and multiple initialization disk candidates, which result from the region class or the region transition uncertainty in the disk profile, are resolved by repeating the labeling step.

2. The method according to claim 1, wherein the farther positions along the spine correspond to positions propagating from the initial position along the spine.

3. The method according to claim 1, wherein the one or more portions of the spine in the image correspond to one or more vertebrae and/or intervertebral discs of the spine in the image.

4. The method according to claim 1, wherein the model of the spine segment relates to anatomical properties of two to five vertebrae and/or intervertebral discs of the spine.

5. The method according to claim 4, wherein the model of the spine segment relates to anatomical properties of three intervertebral discs of the spine.

6. The method according to claim 4, wherein the model of the spine segment relates to anatomical properties of two vertebrae of the spine.

7. The method according to claim 5, wherein the three intervertebral discs of the spine are associated with two vertebrae of the spine.

8. The method according to claim 6, wherein three intervertebral discs of the spine are associated with the two vertebrae of the spine.

9. The method according to claim 1, wherein the initial position of the initial segment of the spine in the image is established by considering anatomical knowledge about spines.

10. The method according to claim 9, wherein the initial position of the initial segment of the spine in the image is established by detecting at least one anatomical landmark of the spine in the image.

11. The method according to claim 10, wherein the at least one anatomical landmark relates to one of a vertebra at a first rib, a vertebra at a last rib, and/or a sacral foramina.

12. The method according to claim 1, wherein the initial position of the initial segment of the spine in the image is established by considering Markov Random Field matching qualities.

13. An apparatus for labeling one or more portions of a spine in an image of a human or animal body, the apparatus comprising:
   an image processing unit configured or programmed to:
   a) match a model of a spine segment with segments of the spine in the image by:
      starting matching the model of the spine segment with an initial segment of the spine in the image, wherein the initial segment of the spine in the image is located at an initial position along the spine in the image; and
      continuing matching the model of the spine segment with one or more further segments of the spine in the image, wherein the further segments of the spine in the image are located at positions farther along the spine in the image, and the model of the spine segment relates to anatomical properties of one or more portions of the spine; and
   b) label the one or more portions of the spine in the image in response to step a), wherein
   the image processing unit is configured or programmed to establish an initial position of an initialization disk of the spine in the image by a disk profile corresponding to a string of region classes to which a set of disk candidates is mapped by classifying each disk candidate of the set of disk candidates to a region class or a region transition uncertainty; and
   the disk profile is matched to a full spine profile and multiple initialization disk candidates, which result from the region class or the region transition uncertainty in the disk profile, are resolved by repeating the labeling of the one or more portions of the spine in the image.

14. A system for labeling one or more portions of a spine in an image of a human or animal body, the system comprising:
   an image acquisition unit configured or programmed to acquire at least one image of at least a portion of a human or animal body; and
   the apparatus according to claim 13.

15. The system according to claim 14, wherein the image acquisition unit is a computed tomography unit.

* * * * *